United States Patent
Schwarz et al.

(10) Patent No.: US 6,583,130 B1
(45) Date of Patent: Jun. 24, 2003

(54) $C_{13}$-SUBSTITUTED ESTRA-1,3,5,(10)-TRIEN-3-YL SULFAMATES, METHODS OF PREPARING SAME, AND PHARMACEUTICAL COMPOSITIONS CONTAINING THESE COMPOUNDS

(75) Inventors: Sigfrid Schwarz, Jena (DE); Gerd Müller, Jena (DE); Dirk Kosemund, Erfurt (DE); Margit Richter, Jena (DE); Olaf Peters, Jena (DE); Ina Scherlitz-Hofmann, Jena (DE); Thomas Michel, Leipzig (DE); Walter Elger, Berlin (DE); Gudrun Reddersen, Jena (DE); Birgitt Schneider, Jena (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/656,359

(22) Filed: Sep. 6, 2000

Related U.S. Application Data
(60) Provisional application No. 60/153,564, filed on Sep. 13, 1999.

(51) Int. Cl.[7] .......................... A61K 31/58; C07J 43/02; C07J 41/02
(52) U.S. Cl. .................. 514/176; 514/182; 540/113; 552/510
(58) Field of Search ................. 514/176, 182; 540/113; 552/510

(56) References Cited

FOREIGN PATENT DOCUMENTS

| DE | 19712488 | 10/1998 |
|---|---|---|
| WO | 9305064 | 3/1993 |
| WO | 9714712 | 4/1997 |
| WO | 9933858 | 7/1999 |

OTHER PUBLICATIONS

Ahmed et al.: "Derivation of a possible transition–state for the reaction catalysed by the enzyme Estrone Sulfatase (ES)", Biorganic & Medicinal Chemistry Letters, GB, Oxford, vol. 9, No. 12, Jun. 12, 1999, pp. 1645–1650.

S. Schwarz et al.: "Synthesis of estrogen sulfamates: Compounds with a novel endocrinological profile" Steroids: Structure, Function, and Regulation, US, Elsevier Science Publishers, New York, N.Y., vol. 61, No. 12, Dec. 1, 1996, pp. 710–717.

Database Chemabs "Online" Chemical Abstracts Service, Columbus, Ohio, U.S., I.B. Sorokina, et al.: "Estrogen and antineoplastic activity in a series of transformed estrone and estradiol analogs"—retrieved from STN Database accession No. 80:91450, XP002160075 abstract & Izv. Akad. Nauk SSSR, Ser Biol. (1973), (5), 664–70.

G. M. Anstead, et al.: "The estradiol phamacophore: Ligand structure–estrogen receptor binding affinity relationships and a model for the receptor binding site" Steroids: Structure, Function, and Regulation, US, Elsevier Science Publishers, New York, N.Y., vol. 62, No. 3, Mar. 1, 1997, pp. 268–303.

A. Purohit et al; Regulation of Aromatase and Sulphatase in Breast Tumour Cells; Journal of Endocrinology 1996; vol. 150; pp. 565–571.

J.Pasqualini et al.; Estrone Sulfatase Versus Estrone Sulfotransferase in Human Breast Cancer: Potential Clinical Applications; Journal of Steroid Biochemistry and Molecular Biology, vol. 69 1999; pp. 287–292.

A. Purohit et al; The Development of A–ring Modified Analogues of Oestrone–3–O–sulphamate as Potent Steroid Sulphatase Inhibitors with Reduced Oestrogenicity; Journal of Steroid Biochemistry and Molecular Biology 1998 Vol. 64, No. 5–6; pp. 269–275.

N.Howarth et al.; Estrone Sulfamates: Potent Inhibitors of Estrone Sulfatase with Therapeutic Potential; J. Med. Chem. 1994, Vol. 37; pp. 219–221.

W.Elger et al.; Sulfamates of Various Estrogens are Prodrugs with Increased Systemic and Reduced Hepatic Estrogenicity at Oral Application; J. Steriod Biochem. Molec. Biol. 1995 Vol. 55, No. 3–4; pp. 395–403.

L. Lawrence Woo et al; Oestrone 3–0–(N–Acetyl) Sulphamate, A Potential Molecular Probe of the Active Site of Oestrone Sulphatase; Bioorganic & Medicinal Chemistry Letters, vol. 7,No. 24, pp. 3075–3080 1997.

*Primary Examiner*—Joseph K. McKane
*Assistant Examiner*—Andrea D. Small
(74) *Attorney, Agent, or Firm*—Norris McLaughlin & Marcus

(57) ABSTRACT

The invention relates to new $C_{13}$-substituted estra-1,3,5(10)-trien-3-yl sulfamates of general formula I,

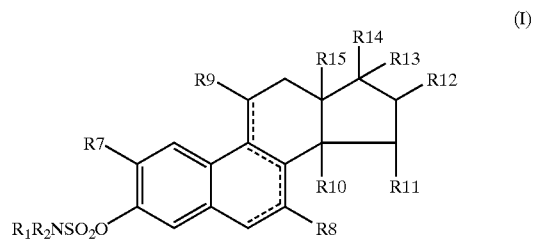

wherein $R_1$ represents an acyl residue, oxycarbonyl residue, aminocarbonyl residue, sulfonyl residue, or aminosulfonyl residue, and $R_{15}$ represents ethyl, methods of preparing same, and pharmaceutical compositions containing these compounds.

The compounds of the invention of general formula I inhibit the activity of steroid sulfatase (EC 3.1.6.2) and do not exhibit any estrogenic effect.

8 Claims, No Drawings

$C_{13}$-SUBSTITUTED ESTRA-1,3,5,(10)-TRIEN-3-YL SULFAMATES, METHODS OF PREPARING SAME, AND PHARMACEUTICAL COMPOSITIONS CONTAINING THESE COMPOUNDS

This application claims the benefit of U.S. Provisional application serial No. 60/153,564 filed Sep. 13, 1999.

BACKGROUND OF THE INVENTION

The invention relates to new estra-1,3,5(10)-trien-3-yl sulfamates having a $C_2$–$C_5$ alkyl, alkenyl or alkynyl residue in $C_{13}$ position and an acyl, oxycarbonyl, aminocarbonyl, sulfonyl, or aminosulfonyl residue on the nitrogen atom of the sulfamate group. The invention is also directed to methods of producing the compounds according to the invention, and to pharmaceutical compositions containing these compounds. The compounds of the invention were found to be steroid sulfatase inhibitors, which exhibit no estrogenic effect.

In the human organism, estrogens are predominantly synthesized and secreted by the ovaries. Accordingly, the estradiol, estrone and estrone sulfate blood levels are subject to fluctuations in sexually mature women during the cycle. During human pregnancy, substantially higher amounts of estrogen are secreted by the placenta compared to the ovary. In addition to these estrogen sources, peripheral estrogen sources play a role in the human organism which, above all, gain importance in those cases where ovarian estrogen secretion has ceased or has not been established yet. As has been demonstrated, these estrogen sources are of major physiological importance in males as well.

Various tissues possess an enzymatic equipment (Purohit A. et al., Regulation of aromatase and sulphatase in breast tumor cells, 150 (1996), p. 65) that causes conversion of adrenal steroids to estrone and estradiol in tissue. Their effect proceeds in an autocrine or paracrine fashion at the site of biosynthesis, and significant estrogen levels do not necessarily have to appear in the blood. Another mechanism by which biologically relevant amounts of estrogen are formed in the tissue is hydrolytic cleavage of estrogen conjugates, particularly estrone sulfate. In this context, the production of estrone in the endometrium and in breast tissue and the tumors proceeding from such tissue is of special pathological importance, because tumor growth can be stimulated in this way. In breast carcinoma, it has been found that the amount of estrogen generated by sulfatase activity (cleavage of estrone sulfate) exceeds that via aromatase by a factor of 50–300 fold (Pasqualini J. R. et al., Estrone sulfatase versus estrone sulfotransferase in human breast cancer: potential clinical applications. J. Steroid Biochem. and Mol. Biol. 69 (1999) 287–292). Similar findings have been gathered by other groups as well. In breast tissue, 10 times more estrone is produced from androstenedione via sulfatase than via aromatase.

Accordingly, the fact can be regarded as proven that sulfatase inhibitors are capable of inhibiting the growth of estrogen-dependent tumors with high efficiency, because they massively reduce the estrogen concentration in the tumor tissue itself.

Under therapeutic aspects, sulfatase inhibitors are therefore the subject of intensified search, which themselves are non-estrogenic and do not yield estrogenic products as a result of hydrolysis. Thus, for example, Purohit A. et al., J. Steroid Biochem. Molec. Biol., Vol. 64, No. 5–6, pp. 269–275 (1998), describe 2-methoxyestrone 3-O-sulfamate to be a potent sulfatase inhibitor that does not exhibit any estrogenic effect on the uterine growth in ovariectomized rats. Estrone 3-O-sulfamates as sulfatase inhibitors have also been described in WO 93/05064. The estrone 3-O-sulfamate with an unsubstituted nitrogen is a strong sulfatase inhibitor (cf., Horwarth et al. in J. Med. Chem. 1994, 37, pp. 219–221, particularly FIG. 3 on page 220). However, this substance also exhibits a strong estrogenic effect, as described by Elger W. et al. in J. Steroid Biochem. Mol. Biol. 55 (1995), pp. 395–403. Other estrone 3-O-sulfamates as sulfatase inhibitors have been disclosed in WO 99/33858. These compounds have no essential estrogenic activity.

Bioorg. & Med. Chem. Lett. 7, 24, 3075–3080 (1997), describes N-acetylestrone 3-O-sulfamate as sulfatase inhibitor. However, this compound has a strong estrogenic effect, exceeding ethynylestradiol with respect to its systemic oral efficacy (cf., WO 97/14712).

Likewise, the DE 197 12 488 A1 describes steroid sulfamates which inhibit steroid sulfatase. The estrogenic effect of these compounds is low or absent. Certain steroid sulfamoyloxy compounds having more than one sulfamate group in their molecules, particularly those which are sulfamoylated in positions characteristic for an estrogenic effect, including substituents or side chains (e.g., in 7 and/or 11 position) which may be located at the periphery of the steroid skeleton, have been described to exhibit a significant increase in sulfatase activity with reduced estrogenic effect. Thus, 3,17-disulfamoyloxy derivatives in particular show good sulfatase activity. According to DE 197 12 488 A1, monosulfamates likewise have good sulfatase inhibition with low estrogenicity, with the exception of A ring sulfamates. As mentioned above, A ring sulfamates are known from WO 97/14712 to be compounds having a distinctly strong estrogenic effect.

SUMMARY OF THE INVENTION

It was the object of the present invention to provide additional steroid sulfatase inhibitors which themselves do not exhibit any estrogenic effect and will not yield any estrogenic products as a result of hydrolysis

DESCRIPTION OF THE PREFERRED EMBODIMENTS

Surprisingly, it was found that new $C_{13}$-substituted estra-1,3,5(10)-trien-3-yl sulfamates of general formula I, their physiologically tolerable salts or eaters,

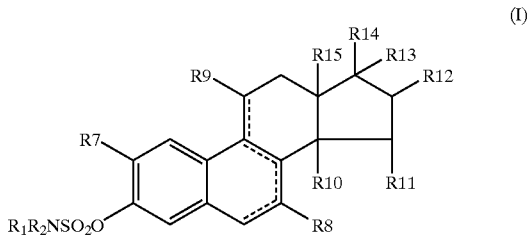

(I)

wherein
  $R_1$ represents $COR_3$, $COOR_4$, $CONR_5R_6$, $SO_2R_4$, $SO_2NR_5R_6$,
  $R_2$ represents hydrogen, $C_1$–$C_{10}$ alkyl, $C_1$–$C_{10}$ alkoxyalkyl, $C_3$–$C_{10}$ cycloalkyl, $C_2$–$C_{10}$ alkenyl, $C_2$–$C_{10}$ alkynyl, aryl, aryl ($C_1$–$C_3$)alkyl, or $C_1$–$C_3$ alkylaryl, $COR_3$; $COOR_4$; $CONR_5R_6$; $SO_2R_4$; $SO_2NR_5R_6$, $R_3$ represents H or $R_4$, $R_4$ represents $C_1$–$C_{17}$ alkyl, $C_1$–$C_{17}$ haloalkyl, $C_2$–$C_{17}$ alkenyl, $C_2$–$C_{17}$ alkynyl, $C_3$–$C_{10}$ cycloalkyl, aryl, aryl ($C_1$–$C_3$)alkyl, $C_1$–$C_3$ alkylaryl, $R_5$, $R_6$ independently represent hydrogen, $C_1$–$C_5$ alkyl, $C_1$–$C_5$ haloalkyl, aryl, aryl($C_1$–$C_3$)alkyl, $C_1$–$C_3$ alkylaryl, or, together with the nitrogen atom to which they are bound, form a polymethyleneimino residue having 2–6 C atoms or a morpholino residue, $R_7$, $R_9$ independently represent H, OH, halogen, $C_1$–$C_5$ alkoxy or $C_1$–$C_5$ haloalkoxy, $R_8$ represents H, OH, $C_1$–$C_5$ alkyl, $C_1$–$C_5$ haloalkyl, $C_2$–$C_5$ alkenyl, $C_2$–$C_5$ alkynyl, or halogen, $R_{10}$, $R_{11}$ represent hydrogen, or $R_{10}$ and $R_{11}$ together represent a $CH_2$ group, $R_{12}$, $R_{13}$, $R_{14}$ independently represent H, OH, $C_1$–$C_5$ alkoxy, or $C_1$–$C_5$ haloalkoxy, or $R_{12}$ represents halogen, or $R_{13}$ and $R_{14}$ together represent oxygen, or together represent a =CXY group wherein X and Y independently represent hydrogen, halogen or a $C_1$–$C_5$ alkyl group, or $R_{13}$, $R_{14}$ independently represent $C_1$–$C_5$ alkyl, $C_2$–$C_5$ alkenyl, or $C_2$–$C_5$ alkynyl, $R_{15}$ represents $C_2$–$C_5$ alkyl, $C_2$–$C_5$ alkenyl or $C_2$–$C_5$ alkynyl, $R_8$, $R_9$, $R_{10}$, $R_{12}$, $R_{13}$, $R_{15}$ independently are in α or β position, and up to 2 additional double bonds may be present in rings B and C, inhibit the activity of steroid sulfatase (EC 3.1.6.2) with extreme efficiency and do not exhibit any estrogenic effect.

In the meaning of the invention, physiologically tolerable salts are alkali or alkaline earth salts, particularly sodium, potassium or ammonium salts.

Conventional, physiologically tolerable inorganic or organic acids which may be esterified with the free hydroxy groups of the compounds of general formula I are e.g. phosphoric acid, sulfuric acid, oxalic acid, maleic acid, fumaric acid, lactic acid, tartaric acid, malic acid, citric acid, salicylic acid, adipic acid, and benzoic acid.

In the meaning of the invention, alkyl represents a branched or unbranched hydrocarbon chain. Accordingly, halozalkyl represents a mono- or polyhalogen-substituted, branched or unbranched hydrocarbon chain. Alkenyl represents a branched or unbranched hydrocarbon chain having at least one double bond. Alkynyl represents a branched or unbranched hydrocarbon chain having at least one triple bond.

Alkoxy represents a branched or unbranched hydrocarbon chain with one or more intervening oxygen atoms. In case of haloalkoxy, the alkoxy residue may be mono- or polysubstituted with halogen.

In the meaning of the invention, aryl represents a phenyl residue which may optionally be substituted, or a heteroaryl residue, e.g. pyridine, picoline, lutidine. collidine, quinoline, acridine, pyridazine, pyrimidine, pyrazine, triazine, pterine, pyrrole, indole, pyrazole, imidazole, 1,2,3-triazole, 1,2,4-triazole, tetrazole, oxazole, thiazole, thiodiazole.

In a particularly preferred embodiment of the invention, $R_2$ represents hydrogen. More preferably, $R_1$ represents an acyl residue, —$COR_3$. In a preferred embodiment, $R_{15}$ represents ethyl or propyl.

Especially preferred compounds of the invention are the following:

1) 17-Oxo-18a-homo-estra-1,3,5(10)-trien-3-yl (N-formyl)-sulfamate
2) 17-Oxo-18a-homo-estra-1,3,5(10)-trien-3-yl (N-acetyl)-sulfamate
3) 17β-Hydroxy-18a-homo-estra-1,3,5(10)-trien-3-yl (N-acetyl)sulfamate
4) 17-Oxo-18a-homo-estra-1,3,5(10)-trien-3-yl (N-propionyl)sulfamate
5) 17β-Hydroxy-18a-homo-estra-1,3,5(10)-trien-3-yl (N-propionyl)sulfamate
6) 17-Oxo-18a-homo-estra-1,3,5(10)-trien-3-yl (N-butyryl)-sulfamate
7) 17α-Hydroxy-18a-homo-estra-1,3,5(10)-trien-3-yl (N-butyryl)sulfamate
8) 17-Oxo-18a-homo-estra-1,3,5(10)-trien-3-yl (N-valeryl)-sulfamate
9) 17β-Hydroxy-18a-homo-estra-1,3,5(10)-trien-3-yl (N-valeryl)sulfamate
10) 17-Oxo-18a-homo-estra-1,3,5(10)-trien-3-yl-(N-hexanoyl)-sulfamate
11) 17β-Hydroxy-18a-homo-estra-1,3,5(10)-trien-3-yl (N-hexanoyl)sulfamate
12) 17-Oxo-18a-homo-estra-1,3,5(10)-trien-3-yl (N-decanoyl)-sulfamate
13) 17-Oxo-18a-homo-estra-1,3,5(10)-trien-3-yl (N-stearoyl)-sulfamate
14) 17-Oxo-18a-homo-estra-1,3,5(10)-trien-3-yl (N-cyclopentanecarbonyl)sulfamate
15) 17-Oxo-14α,15α-methylene-18a-homo-estra-1,3,5(10)-trien-3-yl (N-acetyl)sulfamate
16) 17β-Hydroxy-2-methoxy-18a-homo-estra-1,3,5(10)-trien-3-yl [N-(2,2-dimethyl)propionyl]sulfamate
17) 16α-Fluoro-17β-hydroxy-18a-homo-estra-1,3,5(10)-trien-3-yl (N-acetyl)sulfamate
18) 17β-Hydroxy-7α-methyl-18a-homo-estra-1,3,5(10)-trien-3-yl (N-acetyl)sulfamate
19) 13-Ethyl-17-hydroxy-18,19-dinor-17α-pregna-1,3,5(10)-trien-20-yn-3-yl (N-acetyl)sulfamate
20) 17β-Methoxy-18a-homo-estra-1,3,5(10)-trien-3-yl (N-formyl)sulfamate
21) 17-Oxo-18a-homo-estra-1,3,5(10),8-tetraen-3-yl (N-acetyl)sulfamate
22) 17β-Hydroxy-13-propyl-gona-1,3,5(10)-trien-3-yl (N-acetyl)-sulfamate
23) 17-Oxo-13-propyl-gona-1,3,5(10)-trien-3-yl (N-acetyl)-sulfamate
24) 16α-Fluoro-17-oxo-18a-homo-estra-1,3,5(10)-trien-3-yl (N-acetyl)sulfamate
25) 16β-Fluoro-17-oxo-18a-homo-estra-1,3,5(10)-trien-3-yl (N-acetyl)sulfamate
26) 16α-Fluoro-17β-hydroxy-18a-homo-estra-1,3,5(10)-trien-3-yl (N-acetyl)sulfamate
27) 16α-Fluoro-17α-hydroxy-18a-homo-estra-1,3,5(10)-trien-3-yl (N-acetyl)sulfamate
28) 16β-Fluoro-17β-hydroxy-18a-homo-estra-1,3,5(10)-trien-3-yl (N-acetyl)sulfamate
29) 16β-Fluoro-17α-hydroxy-18a-homo-estra-1,3,5(10)-trien-3-yl (N-acetyl)sulfamate
30) 2-Methoxy-17-oxo-18a-homo-estra-1,3,5(10)-trien-3-yl (N-acetyl)sulfamate
31) 17β-Hydroxy-2-methoxy-18a-homo-estra-1,3,5(10)-trien-3-yl (N-acetyl)sulfamate
32) 2,17β-Dimethoxy-18a-homo-estra-1,3,5(10)-trien-3-yl (N-acetyl)sulfamate 33) 17β-tert-Butoxy-2-methoxy-18a-homo-estra-1,3,5(10)-trien-3-yl (N-acetyl)sulfamate
34) 16α-Fluoro-2-methoxy-17-oxo-18a-homo-estra-1,3,5(10)-trien-3-yl (N-acetyl)sulfamate
35) 16α-Fluoro-17β-hydroxy-2-methoxy-18a-homo-estra-1,3,5(10)-trien-3-yl (N-acetyl)sulfamate
36) 2-Ethoxy-17-oxo-18a-homo-estra-1,3,5(10)-trien-3-yl (N-acetyl)sulfamate
37) 2-Ethoxy-17β-hydroxy-18a-homo-estra-1,3,5(10)-trien-3-yl (N-acetyl)sulfamate
38) 18a-Homo-estra-1,3,5(10)-trien-3-yl (N-acetyl)sulfamate
39) 17-Methylene-18a-homo-estra-1,3,5(10)-trien-3-yl (N-acetyl)sulfamate
40) 17-Difluoromethylene-18a-homo-estra-1,3,5(10)-trien-3-yl (N-acetyl)sulfamate
41) 17-Ethylidene-18a-homo-estra-1,3,5(10)-trien-3-yl (N-acetyl)sulfamate
42) 17-Oxo-18a-homo-13α-estra-1,3,5(10)-trien-3-yl (N-acetyl)sulfamate
43) 17β-Hydroxy-18a-homo-13α-estra-1,3,5(10)-trien-3-yl (N-acetyl)sulfamate
44) 17-Oxo-18a-homo-13α-estra-1,3,5(10),8-tetraen-3-yl (N-acetyl)sulfamate
45) 17-Oxo-18a-homo-estra-1,3,5(10),6,8-pentaen-3-yl (N-acetyl)sulfamate
46) 17-Oxo-18a-homo-estra-1,3,5(10),7-tetraen-3-yl (N-acetyl)sulfamate
47) 17-Oxo-18a-homo-estra-1,3,5(10),8(14)-tetraen-3-yl (N-acetyl)sulfamate
48) 17β-Hydroxy-18a-homo-estra-1,3,5(10)-trien-3-yl (N-trifluoroacetyl)sulfamate
49) 17-Oxo-18a-homo-1,3,5(10)-trien-3-yl (N-nonafluorovaleroyl)sulfamate
50) 17-Oxo-2-trifluoromethoxy-18a-homo-estra-1,3,5(10)-trien-3-yl (N-acetyl)sulfamate Surprisingly, replacement of the $C_{13}$ methyl group which is characteristic for estra-1,3,5(10)-triene derivatives by a $C_2$–$C_5$ alkyl group in 13 position, which optionally may include double or triple bonds, results in complete disappearance of the estrogenic effect without impairing the sulfatase-inhibiting activity of the compounds.

The strong sulfatase-inhibiting activity of the compounds according to the invention becomes manifest in a reduced cleavage of estrone sulfate in organs and tissues of ovariectomized rats. Another characteristic is that the ratio of toluene-extractable metabolites of estrone sulfate in the blood is massively reduced. Therefore, the action pattern of the compounds according to the invention allows their use in the production of drugs for the treatment of estrogen-dependent diseases, namely, for all those therapies where the sulfatase activity is to be inhibited and an estrogenic side effect is undesirable. The treatment of estrogen-dependent tumor diseases may be mentioned as an example.

Therefore, the present invention is also directed to pharmaceutical compositions containing at least one compound of general formula I, optionally together with pharmaceutically tolerable adjuvants and/or vehicles.

Such pharmaceutical compositions and drugs can be used in oral, rectal, vaginal, subcutaneous, percutaneous, intravenous, or intramuscular applications. In addition to conventional vehicles and/or diluents, they contain at least one compound of general formula I.

The drugs of the invention are produced in a well-known fashion using conventional solid or liquid vehicles or diluents and conventionally employed pharmaceutic-technical adjuvants, with a suitable dosage as appropriate for the desired type of application. Preferred formulations consist of an administration form which is suitable for oral application. For example, such administration forms are tablets, film tablets, coated tablets, capsules, pills, powders, solutions or suspensions, or depot forms as well.

Obviously, parenteral formulations such as injection solutions are also possible. Furthermore, suppositories and agents for vaginal application may also be mentioned, for example.

For example, appropriate tablets can be obtained by mixing the active substance with well-known adjuvants, e.g. inert diluents such as dextrose, sugar, sorbitol, mannitol, polyvinylpyrrolidone, disintegrants such as corn starch or alginic acid, binders such as starch or gelatin, lubricants such as magnesium stearate or talc, and/or agents to achieve a depot effect, such as carboxypolymethylene, carboxymethylcellulose, cellulose acetate phthalate, or polyvinyl acetate. The tablets may also be made up of several layers.

Similarly, coated tablets can be produced by coating cores prepared in an analogous fashion as tablets, using agents conventionally employed in tablet coatings, e.g. polyvinylpyrrolidone or shellac, gum arabic, talc, titanium oxide, or sugar. The coating may also consist of multiple layers, where the adjuvants mentioned above in context with the tablets can be used.

Solutions or suspensions including the compounds of the invention of general formula I may additionally contain taste-improving agents such as saccharine, cyclamate or sugars, as well as e.g. flavors, such as vanillin or orange extract. In addition, they may contain suspending aids such as sodium carboxymethylcellulose, or preservatives such as p-hydroxybenzoates.

For example, capsules containing the compounds of general formula I can be produced by mixing the compound(s) of general formula I with an inert vehicle such as lactose or sorbitol and encapsulating in gelatin capsules.

For example, suitable suppositories can be produced by admixing vehicles intended for such purpose, such as neutral fats or polyethyleneglycol or derivatives thereof.

Suitable dosages of the compounds according to the invention are from 0.001 to 10 mg per day, depending on body weight, age and constitution of the patient, and the required daily dose may be applied via single or multiple administrations.

The invention is also directed to a method of producing the compounds of the invention of general formula I

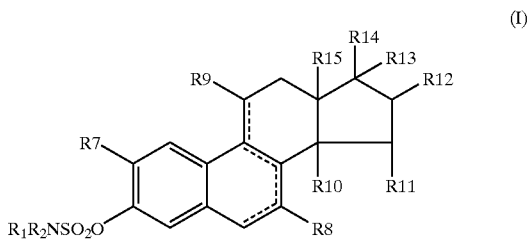

(I)

wherein the residues $R_1$ through $R_{15}$ have the above-specified meanings,
in which method
a) suitable estra-1,3,5(10)-trien-3-yl sulfamate derivatives having residues $R_2$ and $R_7$ through $R_{15}$ as indicated above, which have at least one hydrogen atom on the nitrogen atom of the sulfamate residue, are reacted with a suitable activated carboxylic acid, sulfonic acid or amidosulfonic acid, or a suitable activated carbonic acid monoester or carbonic acid monoamide or b) suitable 3-hydroxy-estra-1,3,5 (10)-triene derivatives having residues $R_7$ through $R_{15}$ as indicated above are reacted with an activated (N—$COR_3$)amidosulfonic acid, (N—$COOR_4$)amidosulfonic acid, (N—$CONR_5R_6$)amidosulfonic acid, (N—$SO_2R_4$) amidosulfonic acid, or (N—$SO_2NR_5R_6$)amidosulfonic acid, in a per se known fashion, optionally in the presence of a base each time, the products thus obtained are optionally reacted further in a suitable manner, and the products thus obtained are optionally converted to physiologically tolerable metal salts or esters.

The 3-hydroxy-estra-1,3,5(10)-triene derivatives having residues $R_7$ through $R_{15}$ are prepared according to methods common in steroid chemistry, such as exemplified in Liebigs Ann. Chem. 702 (1967), 141–148. Estra-1,3,5(10)-trien-3-yl sulfamate derivatives having residues $R_2$ and $R_7$ through $R_{15}$ can be provided in analogy to methods exemplified in Steroids 61 (1996), 710–717.

Without in tending to be limiting, the following examples are to illustrate the invention in more detail.

EXAMPLE 1

17-Oxo-18a-homo-estra-1,3,5(10)-trien-3-yl (N-Acetyl)sulfamate a) 6.0 g (0.021 mol) of 18a-methylestrone and 13.7 ml (0.123 mol) of 2,4,6-collidine were dissolved in 1.45 l of dichloromethane, 18.4 g (0.159 mol) of amidosulfonic acid chloride was added in portions at room temperature, and this was maintained at reflux for 4 hours. The cooled reaction mixture then was washed to neutrality, initially using 3×300 ml of water, then 2×200 ml of saturated sodium hydrogen carbonate solution, and finally water. The organic phase was dried with sodium sulfate, the solvent was distilled off, and the residue was recrystallized from ethyl acetate, thus obtaining 17-Oxo-18a-homo-estra-1,3,5(10)-trien-3-yl sulfamate; m.p.: 180–182° C. (ethyl acetate).

b) 5.5 g of the obtained sulfamate was dissolved in 55.2 ml of pyridine and added with 55.2 ml (0.500 mol) of acetic anhydride at room temperature. The reaction mixture was stirred at room temperature for 15 hours and then poured on crushed ice. The precipitate was filtrated off, washed to neutrality with water, and dried. Recrystallization from acetone/n-hexane afforded the title compound; m.p.: 204–206° C. (acetone/n-hexane).

EXAMPLE 2

17-Oxo-18a-homo-estra-1,3,5(10)-trien-3-yl (N-Propionyl)sulfamate 500 mg of the sulfamate obtained in Example 1a was dissolved in a mixture of 17 ml of dichloromethane and 0.2 ml of triethylamine. 175 mg of 4-dimethylaminopyridine and 3.7 ml of propionic anhydride were successively added, and the reaction mixture was stirred for 20 hours at room temperature. Thereafter, decomposition was effected using dilute aqueous hydrochloric acid. Following removal of the organic phase, the latter was washed with saturated aqueous sodium hydrogen carbonate solution and water, dried over anhydrous sodium sulfate, and concentrated in a vacuum rotatory evaporator. The residue was recrystallized from acetone, thus obtaining the title compound; m.p:. 187–188° C. (acetone; decomposition).

EXAMPLE 3

17-Oxo-18a-homo-estra-1,3,5(10)-trien-3-yl (N-Stearoyl)sulfamate 363 mg of the sulfamate obtained in Example 1a was dissolved in a mixture of 5 ml of pyridine and 5 ml of dichloromethane. This solution was added with 3.63 g of stearic acid chloride with stirring. Stirring was allowed to continue for 22 hours at room temperature, followed by addition of 10 ml of water with ice cooling and stirring for another 24 hours at room temperature. Subsequently, the organic phase was separated and washed successively with 2N aqueous hydrochloric acid, water, 2N aqueous potassium hydroxide solution, and water. Following drying over anhydrous sodium sulfate, the extract was concentrated in a vacuum rotatory evaporator, thereby obtaining the title compound as a light-yellow foam.

EXAMPLE 4

17-Oxo-19a-homo-estra-1,3,5(10)-trien-3-yl (N-Benzoyl)sulfamate 360 mg of the sulfamate obtained in Example 1a was dissolved in a mixture of 5 ml of dichloromethane and 5 ml of benzoyl chloride. Following addition of 1.2 ml of benzoyl chloride with stirring, the mixture was allowed to stand for 70 hours at room temperature. Thereafter, work-up was effected in accordance with Example 3. The crude product obtained was subjected to chromatography on silica gel (eluent: cyclohexane/ethyl acetate=1:2 v/v). In this way, the title compound was obtained as an amorphous solid.

MS (electron impact ionization): 466.4 $(M-H)^+$; 468.3 $(M+H)^+$; 490.6 $(M+Na)^+$.

EXAMPLE 5

Ovariectomized adult rats were treated with dosages of the compounds of the invention between 1 and 300 µg orally. 24 hours after the application, leukocyte and organ homogenates of these animals were examined for their capability of cleaving estrone sulfate. The substances according to the invention inhibited hydrolysis of estrone sulfate in the specified dose range between 50–90%. When treating animals with estrone sulfate 24 hours after the treatment with a substance according to the invention, the products of hydrolysis of the former can be extracted from the plasma after one hour. The substances according to the invention reduce the extractable ratio by about 75%.

EXAMPLE 6

17-Oxo-13a-homo-estra-1,3,5(10)-trien-3-yl (N-Trifluoro-acetyl)sulfamate 363 mg of the sulfamate obtained in Example 1a was dissolved in 4 ml of pyridine. The solution, cooled to −10° C., was added dropwise with 2 ml of trifluoroacetic anhydride with vigorous stirring, whereas the mixture was allowed to heat up to room temperature during addition. Following another 2 hours of stirring, the batch was poured on ice, and the reaction product was taken up in dichloromethane. The extract was washed with dilute hydrochloric acid and several times with water until neutrality, dried over anhydrous sodium sulfate and concentrated to dryness under vacuum. The product obtained was purified by means of flash chromatography on 32 g of silica gel 60 (0.040–0.063 mm) using toluene/chloroform/methanol 40:40:10 as eluent. The title compound could be precipitated in an amorphous form at −10° C. from an acetone solution using n-hexane.

MS (ESI): 458.3 (M−H)$^+$; 939.1 [2(M−H)+Na]$^+$.

$^{19}$F-NMR (CF$_3$COOH/DMSO) : 59.502 ppm.

EXAMPLE 7

17-Oxo-13a-homo-estra-1,3,5(10)-trien-3-yl (N-Cyclopentane-carbonyl)sulfamate 363 mg of the sulfamate obtained in Example 1a was stirred up in 3.5 ml of dichloromethane. This mixture was added with 256 mg of powdered potassium hydroxide, and the steroid underwent dissolution during addition. Subsequently, 0.18 ml of cyclopentanecarboxylic acid chloride was added dropwise within 10 minutes. Stirring was allowed to continue for 2 hours at room temperature, 3 ml of water was added, and this was added with dilute hydrochloric acid to pH make 1. The organic phase was removed, washed with water until neutrality, dried over anhydrous sodium sulfate, and concentrated under vacuum. The residue was purified by means of flash chromatography on silica gel 60 (0.040–0.063 mm) using chloroform/toluene/methanol 25:25:10 as eluent, and the title compound was obtained as a solid resin.

MS (EI) m/z 459.2077 (M$^+$).

What is claimed is:

1. A $C_{13}$-substituted estra-1,3,5(10)-trien-3-yl sulfamate of general formula I,

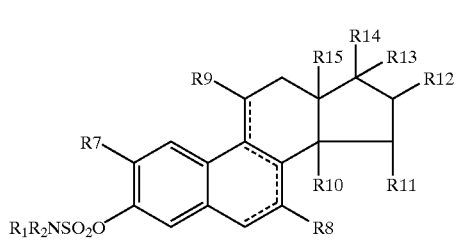

(I)

wherein $R_1$ represents $COR_3$, $COOR_4$, $CONR_5R_6$, $SO_2R_4$, $SO_2NR_5R_6$, $R_2$ represents hydrogen, $C_1$–$C_{10}$ alkyl, $C_1$–$C_{10}$ alkoxyalkyl, $C_3$–$C_{10}$ cycloalkyl, $C_2$–$C_{10}$ alkenyl, $C_2$–$C_{10}$ alkynyl, aryl, aryl($C_1$–$C_3$)alkyl, or $C_1$–$C_3$ alkylaryl, $COR_3$; $COOR_4$; $CONR_5R_6$; $SO_2R_4$; $SO_2NR_5R_6$, $R_3$ represents H or $R_4$, $R_4$ represents $C_1$–$C_{17}$ alkyl, $C_1$–$C_{17}$ haloalkyl, $C_2$–$C_{17}$ alkenyl, $C_2$–$C_{17}$ alkynyl, $C_3$–$C_{10}$ cycloalkyl, aryl, aryl ($C_1$–$C_3$)alkyl, $C_1$–$C_3$ alkylaryl, $R_5$, $R_6$ independently represent hydrogen, $C_1$–$C_5$ alkyl, $C_1$–$C_5$ haloalkyl, aryl, aryl($C_1$–$C_3$)alkyl, $C_1$–$C_3$ alkylaryl, or, together with the nitrogen atom to which they are bound, form a polymethyleneimino residue having 2–6 C atoms or a morpholino residue, $R_7$, $R_9$ independently represent H, OH, halogen, $C_1$–$C_5$ alkoxy or $C_1$–$C_5$ haloalkoxy, $R_8$ represents H, OH, $C_1$–$C_5$ alkyl, $C_1$–$C_5$ haloalkyl, $C_2$–$C_5$ alkenyl, $C_2$–$C_5$ alkynyl, or halogen, $R_{10}$, $R_{11}$ represent hydrogen, or $R_{10}$ and $R_{11}$ together represent a $CH_2$ group, $R_{12}$, $R_{13}$, $R_{14}$ independently represent H, OH, $C_1$–$C_5$ alkoxy, or $C_1$–$C_5$ haloalkoxy, or $R_{12}$ represents halogen, or $R_{13}$ and $R_{14}$ together represent oxygen, or together represent a =CXY group wherein X and Y independently represent hydrogen, halogen or a $C_1$–$C_5$ alkyl group, or $R_{13}$, $R_{14}$ independently represent $C_1$–$C_5$ alkyl, $C_2$–$C_5$ alkenyl, or $C_2$–$C_5$ alkynyl, $R_{15}$ represents ethyl, $R_8$, $R_9$, $R_{10}$, $R_{12}$, $R_{13}$, $R_{15}$ independently are in α or β position, and up to 2 additional double bonds may be present in rings B and C, their physiologically tolerable salts or esters.

2. The compound according to claim 1, wherein $R_1$ represents $COR_3$.

3. The compound according to claim 1, wherein the $R_2$ substituent represents hydrogen.

4. The compound according to claim 1, wherein the $R_{15}$ substituent represents ethyl.

5. The compound according to claim 1, wherein said compounds are selected from the group consisting of:

1) 17-Oxo-18a-homo-estra-1,3,5(10)-trien-3-yl (N-formyl)-sulfamate
2) 17-Oxo-18a-homo-estra-1,3,5(10)-trien-3-yl (N-acetyl)-sulfamate
3) 17β-Hydroxy-18a-homo-estra-1,3,5(10)-trien-3-yl (N-acetyl)sulfamate
4) 17-Oxo-18a-homo-estra-1,3,5(10)-trien-3-yl (N-proprionyl)-sulfamate
5) 17β-Hydroxy-18a-homo-estra-1,3,5(10)-trien-3-yl (N-propionyl)sulfamate
6) 17-Oxo-18a-homo-estra-1,3,5(10)-trien-3-yl (N-butyryl)-sulfamate
7) 17α-Hydroxy-18a-homo-estra-1,3,5(10)-trien-3-yl (N-butyryl)-sulfamate
8) 17-Oxo-18a-homo-estra-1,3,5(10)-trien-3-yl (N-valeryl)-sulfamate
9) 17β-Hydroxy-18a-homo-estra-1,3,5(10)-trien-3-yl (N-valeryl)sulfamate
10) 17-Oxo-18a-homo-estra-1,3,5(10)-trien-3-yl-(N-hexanoyl)-sulfamate
11) 17β-Hydroxy-18a-homo-estra-1,3,5(10)-trien-3-yl (N-hexanoyl)-sulfamate
12) 17-Oxo-18a-homo-estra-1,3,5(10)-trien-3-yl (N-decanoyl)-sulfamate
13) 17-Oxo-18a-homo-estra-1,3,5(10)-trien-3-yl (N-stearoyl)-sulfamate
14) 17-Oxo-18a-homo-estra-1,3,5(10)-trien-3-yl (N-cyclopentanecarbonyl)sulfamate
15) 17-Oxo-14α,15α-methylene-18a-homo-estra-1,3,5 (10)-trien-3-yl (N-acetyl)sulfamate
16) 17β-Hydroxy-2-methoxy-18a-homo-estra-1,3,5(10)-trien-3-yl [N-(2,2-dimethyl)propionyl]sulfamate
17) 16α-Fluoro-17β-hydroxy-18a-homo-estra-1,3,5(10)-trien-3-yl (N-acetyl)sulfamate
18) 17β-Hydroxy-7α-methyl-18a-homo-estra-1,3,5(10)-trien-3-yl (N-acetyl)sulfamate
19) 13-Ethyl-17-hydroxy-18,19-dinor-17α-pregna-1,3,5 (10)-trien-20-yn-3-yl (N-acetyl)sulfamate
20) 17β-Methoxy-18a-homo-estra-1,3,5(10)-trien-3-yl (N-formyl)sulfamate
21) 17-Oxo-18a-homo-estra-1,3,5(10)-tetraen-3-yl (N-acetyl)sulfamate 22) 16β-Fluoro-17-Oxo-18a-homo-estra-1,3,5(10)-trien-3-yl (N-acetyl)sulfamate
23) 16α-Fluoro-17-Oxo-18a-homo-estra-1,3,5(10)-trien-3-yl (N-acetyl)sulfamate
24) 16α-Fluoro-17β-hydroxy-18a-homo-estra-1,3,5(10)-trien-3-yl (N-acetyl)sulfamate
25) 16α-Fluoro-17α-hydroxy-18a-homo-estra-1,3,5(10)-trien-3-yl (N-acetyl)sulfamate
26) 16β-Fluoro-17β-hydroxy-18a-homo-estra-1,3,5(10)-trien-3-yl (N-acetyl)sulfamate
27) 16β-Fluoro-17α-hydroxy-18a-homo-estra-1,3,5(10)-trien-3-yl (N-acetyl)sulfamate
28) 2-Methoxy-17-Oxo-18a-homo-estra-1,3,5(10)-trien-3-yl (N-acetyl)sulfamate
29) 17β-hydroxy-2-methoxy-18a-homo-estra-1,3,5(10)-trien-3-yl (N-acetyl)sulfamate
30) 2,17β-Dimethoxy-18a-homo-estra-1,3,5(10)-trien-3-yl (N-acetyl)sulfamate
31) 17β-tert-Butoxy-2-methoxy-18a-homo-estra-1,3,5(10)-trien-3-yl (N-acetyl)sulfamate
32) 16α-Fluoro-2-methoxy-17-Oxo-18a-homo-estra-1,3,5(10)-trien-3-yl (N-acetyl)sulfamate
33) 16α-Fluoro-17β-hydroxy-2-methoxy-18a-homo-estra-1,3,5(10)-trien-3-yl(N-acetyl)sulfamate
34) 2-Ethoxy-17-Oxo-18a-homo-estra-1,3,5(10)-trien-3-yl (N-acetyl)sulfamate
35) 2-Ethoxy-17β-hydroxy-18a-homo-estra-1,3,5(10)-trien-3-yl (N-acetyl)sulfamate
36) 8a-Homo-estra-1,3,5(10)-trien-3-yl (N-acetyl)sulfamate
37) 17-Methylene-18a-homo-estra-1,3,5(10)-trien-3-yl (N-acetyl)sulfamate
38) 17-Difluoromethylene-18a-homo-estra-1,3,5(10)-trien-3-yl (N-acetyl)sulfamate
39) 17-Ethylidene-18a-homo-estra-1,3,5(10)-trien-3-yl (N-acetyl)sulfamate
40) 17-Oxo-18a-homo-13α-estra-1,3,5(10)-trien-3-yl (N-acetyl)sulfamate
41) 17β-Hydroxy-18a-homo-13α-estra-1,3,5(10)-trien-3-yl (N-acetyl)sulfamate
42) 17-Oxo-18a-homo-13α-estra-1,3,5(10)-tetraen-3-yl (N-acetyl)sulfamate
43) 17-Oxo-18a-homo-estra-1,3,5(10),6,8-pentaen-3-yl (N-acetyl)sulfamate
44) 17-Oxo-18a-homo-estra-1,3,5(10)-7-tetraen-3-yl (N-acetyl)sulfamate
45) 17-Oxo-18a-homo-estra-1,3,5(10),8(14)-tetraen-3-yl (N-acetyl)sulfamate
46) 17β-Hydroxy-18a-homo-estra-1,3,5(10)-trien-3-yl (N-trifluoroacetyl)sulfamate
47) 17-Oxo-18a-homo-1,3,5(10)-trien-3-yl (N-nonafluorovaleroyl)sulfamate; and
48) 17-Oxo-2-trifluoromethoxy-18a-homo-estra-1,3,5(10)-trien-3-yl (N-acetyl)sulfamate.

6. A method of preparing a compound of general formula I,

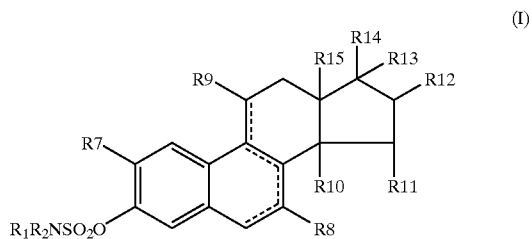

wherein the residues $R_1$ through $R_{15}$ have the meanings specified in claim 1,
in which method
a) suitable estra-1,3,5(10)-trien-3-yl sulfamate derivatives having residues $R_2$ and $R_7$ through $R_{15}$ as indicated above, which have at least one hydrogen atom on the nitrogen atom of the sulfamate residue, are reacted with a suitable activated carboxylic acid, sulfonic acid or amidosulfonic acid, or a suitable activated carbonic acid monoester or carbonic acid monoamide or
b) suitable 3-hydroxy-estra-1,3,5(10)-triene derivatives having residues $R_7$ through $R_{15}$ as indicated above are reacted with an activated (N—$COR_3$)amidosulfonic acid, (N—$COOR_4$)amidosulfonic acid, (N—$CONR_5R_6$)amidosulfonic acid, (N—$SO_2R_4$) amidosulfonic acid, or (N—$SO_2NR_5R_6$)amidosulfonic acid.

7. A pharmaceutical composition, comprising at least one compound according to claim 1, in a pharmaceutically acceptable carrier.

8. A pharmaceutical composition comprising the compound of claim 1, wherein the compound is in the form of at least one physiologically tolerable metal salt or ester.

* * * * *